United States Patent [19]
Comparetto

[11] Patent Number: 5,147,364
[45] Date of Patent: Sep. 15, 1992

[54] OSTEOTOMY SAW/FILE, CUTTING GUIDE AND METHOD

[75] Inventor: John E. Comparetto, Cincinnati, Ohio

[73] Assignee: Ohio Medical Instrument Company, Cincinnati, Ohio

[21] Appl. No.: 486,815

[22] Filed: Mar. 1, 1990

Related U.S. Application Data

[60] Continuation-in-part of Ser. No. 308,257, Feb. 8, 1989, Pat. No. 4,952,214, which is a continuation-in-part of Ser. No. 841,948, Mar. 20, 1986, abandoned, which is a continuation-in-part of Ser. No. 749,475, Jun. 27, 1985, Pat. No. 4,664,102, and Ser. No. 721,640, Apr. 10, 1985, Pat. No. 4,708,133, and Ser. No. 667,424, Nov. 1, 1984, Pat. No. 4,632,102, which is a division of Ser. No. 294,653, Aug. 20, 1981, Pat. No. 4,501,268.

[51] Int. Cl.[5] .............................................. A61F 5/04
[52] U.S. Cl. ....................................... 606/85; 606/84; 606/82; 606/87
[58] Field of Search .................... 29/78; 30/144, 166.3; 606/86, 87, 79, 80, 82, 84, 85

[56] References Cited

U.S. PATENT DOCUMENTS

| | | | |
|---|---|---|---|
| 21,411 | 9/1858 | Forman | 33/26 |
| 352,083 | 11/1886 | Custer | 29/78 |
| 358,026 | 2/1887 | Emerson | 29/78 |
| 2,823,709 | 2/1958 | Konieczka | 83/745 |
| 3,815,599 | 6/1974 | Deyerle | 606/85 |
| 4,069,824 | 1/1978 | Weinstock | 128/317 |
| 4,150,675 | 4/1979 | Comparetto | 128/305 |
| 4,335,715 | 6/1982 | Kirkley | 128/92 VY |
| 4,433,681 | 2/1984 | Comparetto | 128/92 VY |
| 4,501,268 | 2/1985 | Comparetto | 128/92 VY |
| 4,502,474 | 3/1985 | Comparetto | 128/92 VY X |
| 4,509,511 | 4/1985 | Neufeld | 128/92 VY |
| 4,608,898 | 9/1986 | Volk | 83/745 |
| 4,625,725 | 12/1986 | Davison et al. | 29/78 X |
| 4,627,425 | 12/1986 | Reese | 128/92 VY |
| 4,632,102 | 12/1986 | Comparetto | 128/92 VY |
| 4,664,102 | 5/1987 | Comparetto | 128/92 VY |
| 4,708,133 | 11/1987 | Comparetto | 128/92 VY |
| 4,777,942 | 10/1988 | Frey et al. | 606/85 X |

FOREIGN PATENT DOCUMENTS

| | | | |
|---|---|---|---|
| 26410 | 7/1902 | Switzerland | 29/78 |
| 568769 | 4/1945 | United Kingdom | 33/565 |

OTHER PUBLICATIONS

American V. Mueller, Orthopaedic Instruments, p. 1146, 1980.
Amico, Surgical Instruments, p. 343, 1966.
The Osteoguide System, J. E. Comparetto, Comparetto Ideas, Inc.

*Primary Examiner*—Robert A. Hafer
*Assistant Examiner*—Kerry Owens
*Attorney, Agent, or Firm*—Wood, Herron & Evans

[57] ABSTRACT

A method and apparatus for performing arcuate osteotomies wherein a wedge-shaped correction is filed rather than sawed from the bone. A combined saw and file for use in the method has a curved blade with teeth along a longitudinal edge for making an arcuate cut in the direction perpendicular to the edge, and file teeth on one or both of its curved faces for filing out the correction. The effective width of the the blade determines the tip width of the correction; the thickness of the blade determines the width of the arcuate kerf; and the radius of curvature of the blade determines the radius of the arcuate cut. Also disclosed is cutting guide for guiding a saw/file or other cutting implement to make the arcuate cut and the correction.

31 Claims, 2 Drawing Sheets

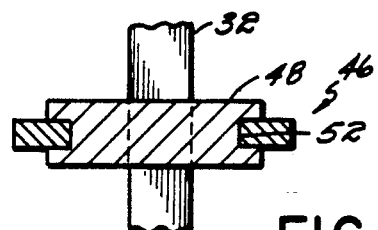
FIG. 7
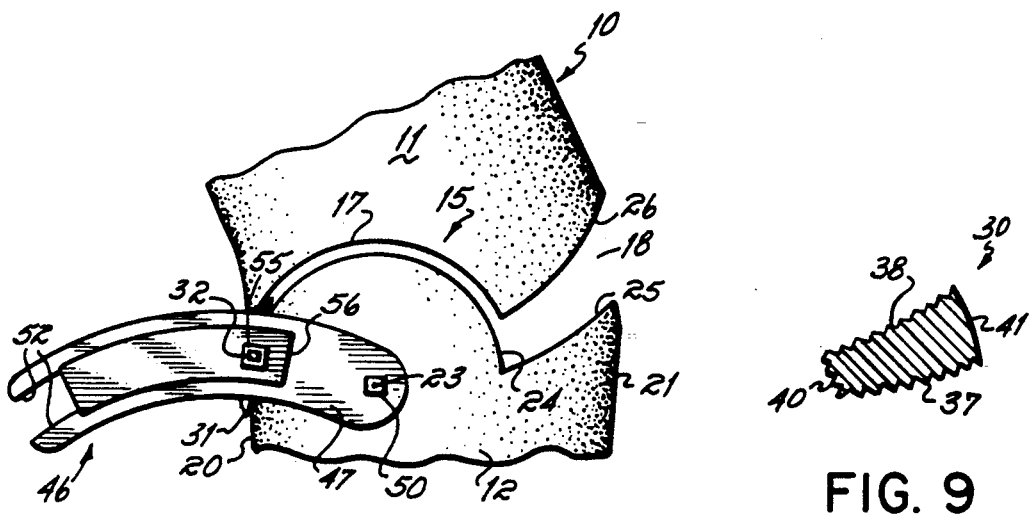
FIG. 8
FIG. 9
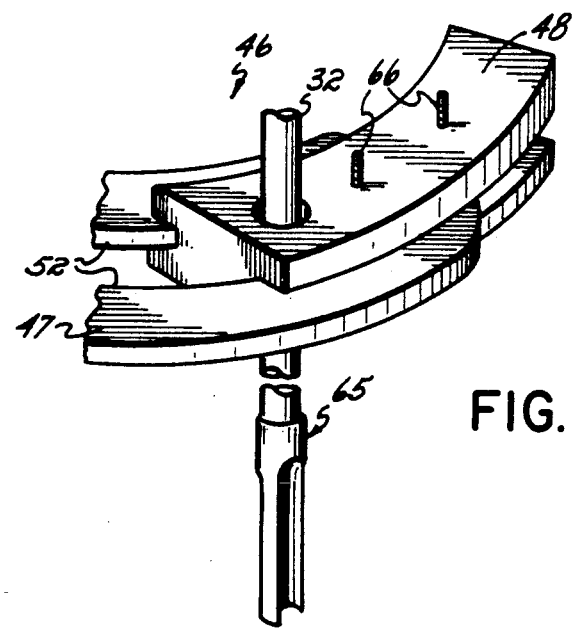
FIG. 10

1

OSTEOTOMY SAW/FILE, CUTTING GUIDE AND METHOD

RELATED INVENTIONS

This application is a continuation-in-part of my copending application Ser. No. 07/308,257, filed Feb. 8, 1989, titled "Arcuate Osteotomy Blade, Blade Guide, and Cutting Method," now U.S. Pat. No. 4,952,214, which was a continuation-in-part of my application Ser. No. 06/841,948, titled "The X-Osteoguide, and Arcuate Bone Cutters," filed Mar. 20, 1986, now abandoned, which was in turn a continuation-in-part of application Ser. No. 06/749,475, titled "Electronic Guidance for Bone Wedge Excision," filed Jun. 27, 1985, now U.S. Pat. No. 4,664,102; and of application Ser. No. 06/721,640, titled "Arcuate Bone Cutter and Wedge Guide System," filed Apr. 10, 1985, now U.S. Pat. No. 4,708,133; and a continuation-in-part of application Ser. No. 667,424, filed Nov. 1, 1984, now U.S. pat. No. 4,632,102, issued Dec. 30, 1986, which was in turn a division of application Ser. No. 294,653, filed Aug. 20, 1981, now U.S. Pat. No. 4,501,268, issued Feb. 26, 1985.

FIELD OF THE INVENTION

This invention relates to surgical techniques and instruments, and more specifically to methods and apparatus for performing arcuate osteotomies.

BACKGROUND

An osteotomy is a surgical procedure for straightening bones wherein the bone is cut transversely and a corrective segment having a tapered or wedge shape is removed from the outside of an undesired bend in the bone. After the corrective segment has been removed the bone segments are brought together to close the wedge-shaped gap left by the removed segment, thereby straightening the bone, which knits in the new orientation. In an arcuate osteotomy, rather than removing a corrective segment across the entire width of the bone, the correction extends only partially across the width of the bone, to an arcuate cut which extends across the rest of the width of the bone. The correction is wider (in the direction longitudinally of the bone) than the kerf of the arcuate cut, and its width and taper determine the amount of correction or straightening. Removal of the correction leaves a gap to one side of the pivot; the opposite bone segments are repositioned around the arcuate cut to close the correction gap and thereby straighten the bone. The technique provides cuts with comparatively long abutting areas, which improves bone knitting. Further discussion of the arcuate osteotomy technique is set forth in my prior U.S. Pat. No. 4,501,268, issued Feb. 26, 1985, to which reference may be had.

My patent application Ser. No. 07/308,257, previously referred to, in a preferred embodiment discloses a technique wherein the arcuate cut is made with a semicircularly curved saw blade. The blade has saw teeth along a longitudinal edge, parallel to its axis of curvature. The blade is guided to cut the desired arc in the bone by a guide having a curved slot along which the blade is advanced, the curved cross-sectional shape of the blade helping the blade to track in its own kerf. Once the arcuate cut has been made, the correction is then cut in three steps. A first correction cut, which will define one side of the wedge-shaped correction, is made from the opposite bone side to the inner end of the arc, but only partially through the thickness of the bone so that the bone is not altogether severed. Using the first correction cut as a guide, a second correction cut is then made at a desired longitudinal spacing from it. This second cut is made through the entire thickness of the bone, thereby severing the bone into two segments. The two correction cuts define a tapered wedge between them which extends from the side of the bone to the arcuate cut. In the third step the first correction cut is then completed through the thickness of the bone, thereby freeing the wedge which is removed. The two bone segments are articulated about the arc to close the gap and straighten the bone. The reason for making the first correction cut through only a part of the thickness of the bone is that if it were cut through the entire thickness, the bone would be severed before the second correction cut had been made, which would make it more difficult to properly position and make the second correction cut. By making the first cut only partial, it can be used as a guide to more precisely position the second cut.

It can be seen that the arcuate technique described is relatively complicated in that it requires three separate steps to define and remove the wedge: the incomplete first correction cut, the second correction cut, and a third cut along the line of the first cut to free the correction wedge.

BRIEF DESCRIPTION OF THE INVENTION

This invention both facilitates the arcuate osteotomy procedure and makes it more precise by simplifying the making of the correction, i.e., the cutting and removal of the correction wedge. In accordance with one aspect of the method of this invention the correction is filed as a kerf of desired width and taper, rather than removed by multiple saw cuts. The "filed" correction can, if desired, be filed outwardly from the inner end of a previously cut arc, to the side of the bone, or it can be filed inwardly from the side of the bone. This greatly facilitates making the correction where the side of the bone is inaccessible or where another factor hinders access to cutting from the side in. The arcuate cut can be made either before or after the correction has been filed.

The new procedure can be carried out using an osteotome chisel or by using a curved saw blade, for example as shown in my previously identified application Ser. No. 308,257, to make the arcuate cut, and by using a conventional file to make the correction. However, I have invented a combined curved saw and file, which is referred to herein as a "saw/file," by which both the arcuate cut and the correction can be made sequentially without even removing the saw/file from the cut. The saw/file has a semicircularly curved blade with teeth along one or both longitudinal edges for making the arcuate cut, and has file teeth on its curved (convex or concave) face for filing the correction. The radius of curvature of the blade corresponds to the desired radius of curvature of the arcuate cut. The arcuate curve is made by reciprocating the blade parallel to its cutting (longitudinal) edge; as it cuts a kerf its curved blade tracks in the kerf. The correction is filed by moving the blade transversely (perpendicularly or angularly) to its axis of curvature, while reciprocating it longitudinally.

Also provided is a cutting guide for guiding a saw/-file or other type of bone cutting implement to make a correction cut, either with or without an arcuate cut.

The guide includes a swing arm which is mountable to a bone for swinging movement around a pivot pin fixed in the bone, and a slide which is movable along the swing arm toward or away from the pivot pin. The slide has means for holding the saw/file or other cutting implement perpendicularly to the bone for cutting. A cutting implement, which can be either reciprocating or rotary for use with the guide, cuts a circular (arcuate) kerf when the swing arm is swung about the pivot, and cuts a correction kerf when the slide is translated inward or outward along the swing arm. The guide preferably includes means for controlling the path of the cutting implement to make precisely angulated cuts which will define a correction of desired taper.

DESCRIPTION OF THE DRAWINGS

The invention can best be further described by reference to the accompanying drawings, in which

FIG. 7 is an enlarged cross-sectional view of the slide and pivot arm, taken on line 7—7 of FIG. 6;

FIG. 8 is a diagrammatic view similar to FIG. 6 but shows the guide and saw/file at the completion of the arcuate cut, the correction having first been cut;

FIG. 9 is a cross-sectional view of an alternative form of file having a tapered cross-section; and FIG. 10 is a fragmentary perspective view of a cutting implement in the form of a high speed rotary burr, in the cutting guide.

DETAILED DESCRIPTION

Figure 1:
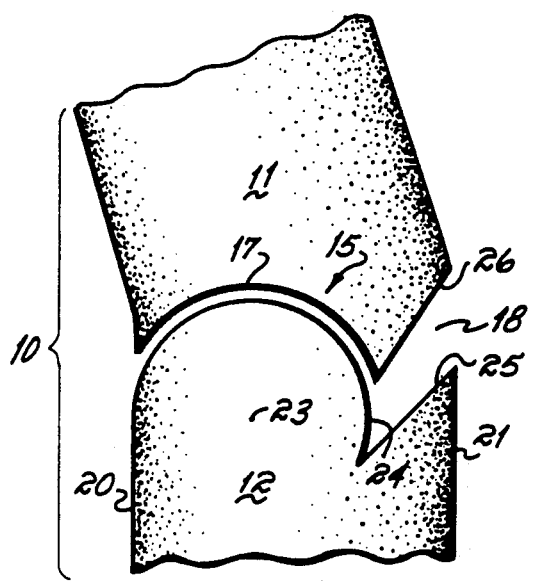
FIG. 1 is an enlarged diagrammatic view of a portion of a bone on which an arcuate osteotomy has been performed, showing the two severed bone segments prior to realignment for straightening the bone.

FIG. 1 schematically illustrates a portion of a bone 10 which has been severed into two segments 11 and 12 by an arcuate osteotomy designated generally by 15. The osteotomy includes an arcuate cut 17 having an inner end which joins a correction cut 18. As can be seen, the opposite sides 25 and 26 of correction 18 lie at an angle to one another while they are cut, but as will be described, when the bone segments 11 and 12 are articulated, the sides 25 and 26 come into parallelism and facially engage one another when the correction is closed. The arcuate cut 17 extends from one side 20 of the bone toward the other side 21; usually the arcuate cut extends across at least 50% but not generally more than about 75% of the width of the bone. It is generally semicircular, being centered about an imaginary axis 23 which is in a plane perpendicular to the axis of the bone. The correction 18 extends from side 21 of the bone to the inner end 24 of the correction.

FIG. 1 shows side 25 of correction 18 as extending at a sharp angle, about 45°, to the side 21 of the bone, but in principal the cut side 25 can be perpendicular to the bone side or at any desired angle, up to roughly 135°. Generally, where the size of the bone and operating conditions permit, I prefer to make the correction at an angle approximately as shown, because for a given arcuate cut the greater the angulation of the correction, the longer its sides 25 and 26, which in turn promotes firmer seating of the severed pieces in the straightened alignment with resultant greater strength.

It should be noted that the "width" of the arcuate cut 17 (as measured along a radius from pivot axis 23) is smaller than the width of the correction wedge (measured where the latter meets the arcuate cut), otherwise the bone would merely be shortened rather than straightened. The greater the width of the correction in relation to the width of the arcuate cut 17, the greater the amount of change in the alignment of the bone segments.

In carrying out an arcuate osteotomy it may be more difficult in a given case, depending upon the size and location of the bone and other adjacent tissues and conditions, to cut from one side of the bone rather than the other side. If for example delicate neurovascular tissue or muscular attachment lies adjacent the desired position of correction 18, that factor hinders cutting inwardly from side 21 toward arcuate cut 17. In such case it is desirable to cut the correction 18 outwardly from the inner end 24 of the arc so as to minimize damage to such adjacent tissue. If delicate structure lies on side 20 for example, then the correction cut would be the initiating inward cut, ending with the breakthrough outwardly of the arcuate cut to bone side 20.

Figure 2:
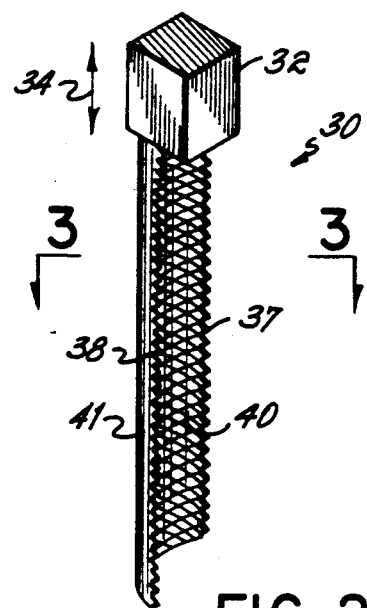
FIG. 2 is a fragmentary perspective view of a saw/file in accordance with a preferred embodiment of the invention.
Figure 3:
FIG. 3 is a cross-sectional view taken on line 3—3 of FIG. 2

FIGS. 2 and 3 illustrate a preferred form of saw/file 30 in accordance with the invention. This instrument functions as both a saw for cutting the arcuate cut 17 and as a file for filing the correction 18. The saw/file 30 has a blade 31 and an elongated shank 32 or other gripping means. Shank 32 is preferably squared (or not round), and in use is engaged by a motor drive, not shown, which reciprocates the saw/file in the longitudinal direction, indicated by arrow 34, i.e., parallel to the (longitudinal) axis of curvature. The shank is preferably centered along the width of the blade.

Blade 31 has a semicircular cross-sectional shape, i.e., its cross section lies on a curve of constant radius, with a first face 40 which is concave and a reverse second face 41 which is convex. It has bone cutting teeth on one or the other, or both, of its longitudinal edges 37 and 38, which are parallel to the axis of shank 32. In the embodiment shown the blade has bone cutting teeth on both of its edges for cutting, so it may be used to cut the arcuate cut in either direction, i.e., clockwise or counterclockwise. These teeth can be either saw teeth (with a set) or file teeth (without a set). Edgewise cutting with these teeth is referred to herein as "sawing" because it forms a narrower kerf, in comparison to the wider correction kerf, regardless of whether the edge teeth are technically saw teeth or file teeth.

In addition to the teeth along the longitudinal edges, the blade also is cut or scored as a file on either its concave (inside) face 40 or its convex (outside) face 41, or both. For a reason to be explained, it is preferred to provide a file surface on only one of the curved faces 40 and 41. I presently prefer to form the file surface on the concave surface, as shown in FIG. 2.

Files intended for use in connection with bone surgery are known. However, the surgeon has had to manually guide those files, a method which is not able to precisely remove bone in a specific correction geometry. Moreover, it has not been possible to make both the arcuate cut and the correction cut with previous files.

Figure 4:
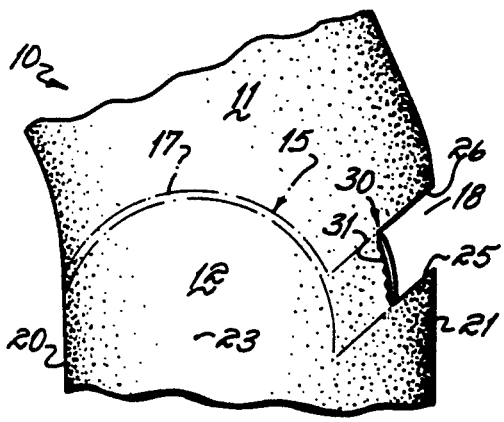
FIG. 4 is a diagrammatic view of a bone on which an arcuate osteotomy is being performed in accordance with a preferred practice of the method of the invention, showing the relative positions of the file saw for making the arcuate cut and the correction.

FIG. 4 illustrates how the saw/file 30 of this invention can be used both to make the arcuate cut and to file the correction. In FIG. 4, it can be seen that the arcuate cut can be made by engaging edge 37 of the saw/file at side 20 of the bone, and proceeding to cut the arc 17. As this occurs, the curved blade tends to track in its own kerf so as to cut an arc corresponding to its own radius of curvature. In making this cut the cutting action is at the leading edge of the blade. However, file teeth on the face of the blade could abrade the bone while the arcuate cut is being made, and thereby undesirably widen or misform the arcuate cut. In order to provide a thinner arcuate kerf, I prefer to provide file teeth on only one face, preferably concave face 40 of blade 31. Thus, this concave face file can be used to file the correction inwardly from the outside of the bone.

Figure 5:
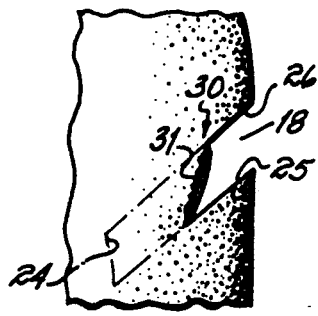
FIG. 5 shows a method of filing a correction narrower than the width of the file.

When an arc of desired length has been cut, blade 31 is then guided to cut in a direction transverse to its concave or convex filing face, between the other bone side 21 and the end of the arcuate cut, to form the correction 18. As used in reference to the filed cut, "transverse" is meant in the broad sense of "crosswise" including but not limited to cutting perpendicularly to faces 40 and 41 as well as other crosswise angles. In the embodiment shown for purposes of explanation, the filing action takes place on the concave face 41 of the blade, from side 21 inward to the arcuate cut. The width of the correction can be less than the actual width of the blade if the blade is held skewed or not perpendicular to the direction of filing, as shown in FIG. 5. If a narrower kerf is desired, the angle of attack of the file can be made sharper.

Figure 6:
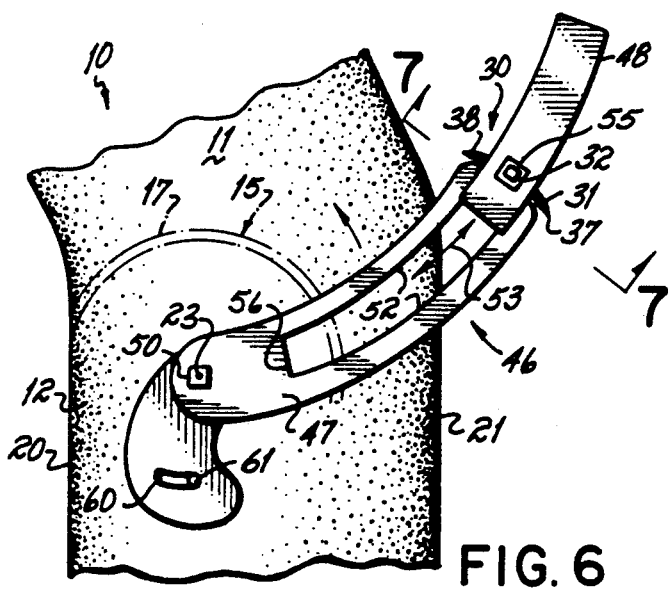
FIG. 6 is a diagrammatic plan view of a cutting guide in accordance with a second aspect of the invention, being used to guide the path of a saw/file to file a curved correction, prior to sawing an arcuate cut in a bone.

Because a circularly curved blade tends to track in its own kerf, it is not always necessary to use a guide to guide the arcuate cutting action of the blade, particularly on smaller bones. However, to minimize any tendency of the saw/blade or other cutting implement to wander or cut a wider kerf than desired, and to provide a precise geometry for either or both cuts, I have invented a cutting guide 46, a preferred form of which is shown in FIG. 6.

Guide 46 comprises a swing arm 47 and an interfitting slide 48 which is slidable along a guide track on or in the arm, such as a slot 52. The arm is swingable about a pivot pin 50 which can be secured to the bone at the desired axis 23, to provide a pivot. In the embodiment shown, slide 48 tracks in a length-wise slot 52 in the arm, as indicated by the arrow 53. Slide 48 preferably is embraced between the sides of slot 52 in arm 47, as shown in FIG. 7. (Rather than sliding in a slot, as shown, the slide can telescope over the arm, or roll along a track.) Slot 52 may be curved so that a curved correction cut 18 will be made, however, a straight slot and correction are also contemplated.

The shank 32 of the blade passes through a guide hole in slide 48, and the slide holds the blade perpendicularly to the guide. To insure constancy of blade angle of attack in making the correction cut, the shank (or a portion of the motor drive, not shown) is preferably square or at least not round, and fits in a correspondingly shaped sleeve or holder 55 in slide 48. The angle or orientation of the blade with respect to the side of cut 18 can be fixed and set at a desired angle, to cut a narrower kerf, by adjusting the orientation of sleeve 55, see FIG. 5. With a vertically reciprocating drive motor energized, slide 48 is moved inwardly along slot 52 and the blade files the kerf inwardly from side 21 of the bone. In the embodiment illustrated the concave face 40 of the blade files the correction. The correction cut should extend inwardly to a position such that the distance from the concave face of the blade 40 to pivot pin 50 substantially equals the radius of curvature of the concave surface 48 of the blade.

As has been described, the sides 25 and 26 of the correction cut 18 must be cut with an angle between them, so that when the bone segments 11 and 12 are thereafter rotated about pivot 23 the sides of correction 18 will come into parallel, face-to-face engagement. The slot 52 in pivot arm 47 has parallel sides which precisely guide the movement of the slide and cutting implement to form each sidewall. Thus, at a given angular position of swing arm 46, movement of the cutter will form a cut with parallel sides rather than forming the desired wedge-shape. In order to form a wedge-shaped correction, it is desirable to provide pivot arm 47 with a cross slot 60, through which a swing limiting second pin or stop 61 projects. Stop 61 is inserted through slot 60 and secured in the bone when the correction is to be cut. Swing arm 47 can then rotate about pivot 50 only within the angular limits established by the points at which the stop 61 abuts the opposite ends of slot 60. To cut side 25 of the correction, the pivot arm is held with stop 61 engaged with one end (the right end in FIG. 6) of slot 60; then when side 25 has been cut, the swing arm is rotated until stop 61 engages the other end of slot 60 (the left end in FIG. 6), and the other side 26 of the correction is formed. The taper of the correction corresponds to the angle subtended by the swing of the swing arm between these limiting positions. Different effective lengths of slot 60 and/or stops 61 of different diameters can be provided for tapers of different amounts. A slot 60 could be provided on either or both sides of pin 50, to facilitate implacement of stop 61.

In the embodiment shown the slot 60 is provided in a J-shaped extension of swing arm 51, on the opposite side of pivot pin 50 from slot 52. This permits stop 61 to be secured near the midline of the bone, but this is not essential if the bone is wide.

Another way to provide a tapered correction is with a file having converging or tapered sides. The sides may be curved, as shown in FIG. 9, or straight. Because of its thickness, this file is not suitable as a saw but it is useful to file a taper on a correction cut with parallel sides, or to file the entire correction.

The arcuate cut is made by edgewise movement of the saw/file. For this purpose stop 61 is removed (if the correction was cut first), slide 48 is held at its inward limit 56 and pivot arm 47 is pivoted about pin 50 to cut the arcuate kerf as designated by the phantom line in FIGS. 4 and 6. The pivotal movement of arm 47 extends the arcuate cut between the correction and the opposite side of the bone (FIG. 7). The guide, pivot, and blade are then removed. The two bone segments 11 and 12 are brought into abutment and reoriented to engage the opposite sides 25 and 26 of the correction cut with one another. The operation may be completed in accordance with conventional practice.

While the guide shown in FIGS. 6 through 8 is especially useful to guide the cutting action of the saw/file which is disclosed herein, it is also useful with other types of bone cutting implements to form precise arcuate osteotomy cuts. For example, it is useful with pneumatically driven rotary cutting apparatus of the type sold by Midas Rex Pneumatic Tools, Inc. Such apparatus uses bone cutting implements called bits or "burrs." Some burrs have cutting edges parallel to their axis and cut perpendicularly to their axes, similar to slot routing bits. Other types of burrs have cross cutting teeth, much like a rasp. As shown in FIG. 10, such a rotary burr 65 may be used in place of the saw/file in slide 48. The burr passes through an oversize opening in the slide; the burr drive (which may be a high speed pneumatic drive) can be secured to slide 48 by mounting means such as the screws 66 shown. A rotary burr 65 tends to cut a kerf wider than a file saw does, and so forms a relatively wide arcuate cut. However, burrs are available in diameters as small as 3/32 and ⅛ inches, and are useful for performing osteotomies on a larger bone such as the tibia. Even if an arcuate cut is made with another type of bone saw, the guide is useful to enable a rotary or cross cutting burr to be used to make correction cuts at precise angulation to one another.

Having described the invention, what is claimed is:

1. An osteotomy saw/file comprising:
    a semicircularly curved blade of uniform thickness having first and second faces on opposite sides thereof and first and second longitudinal edges between said faces,
    at least one of said faces comprising a file having teeth for filing a kerf in a bone in a direction transverse to said face,
    said first edge having teeth formed thereon for cutting edgewise through a bone to make an arcuate cut having a curvature corresponding to that of said blade, and
    a shank for engagement by a drive motor to apply reciprocating motion to said blade,
    the described configuration of said blade thereby enabling an arcuate osteotomy including both a correction cut and an arcuate cut to be performed without removing the blade from a bone, the blade filing a correction cut as a kerf when the blade is advanced in a bone in a direction transverse to said one face and sawing an arcuate cut when advanced circumferentially in a bone along the circumference of said blade.

2. An osteotomy saw/file in accordance with claim 1 wherein,
    said blade has a semi-circular cross sectional shape, said first face being concave and said second face being convex.

3. An osteotomy saw/file in accordance with claim 2 wherein said first face is concave and comprises said file.

4. An osteotomy saw/file in accordance with claim 2 wherein said second face is convex and comprises said file.

5. An osteotomy saw/file in accordance with claim 1 wherein said shank is elongated and has an axis parallel to said first edge.

6. An osteotomy saw/file in accordance with claim 1 wherein said shank is centered with respect to said first and second edges.

7. An osteotomy file for filing a transversely tapered correction in a bone,
    said file having a blade with first and second faces on opposite sides thereof,
    said faces being angulated to one another,
    each said face comprising a film having teeth for filing a bone,
    the angulation of said faces defining a taper for filing a correction in an osteotomy
    said blade having no taper in its longitudinal direction thereby being adapted to cut on both said faces simultaneously, to form a correction slot which is tapered transversely but not longitudinally.

8. An osteotomy instrument comprising a bone file and a guide for controlling the path of filing movement of said file in a bone,
    said file comprising,
    a blade having first and second faces on opposite sides thereof and first and second longitudinal edges between said faces,
    at least one of said faces having teeth for filing a kerf in a direction transverse to said face when reciprocated, and
    a shank for engagement by drive means to apply reciprocating motion to said blade;
    said guide comprising, means mountable to a bone to guide said file for filing a kerf in the form of a slot of uniform width and extending in a direction transverse to said one face.

9. An osteotomy instrument comprising a bone file and a guide for controlling the path of filing movement of said file in a bone,
    said file comprising,
    a blade having first and second faces on opposite sides thereof and first and second longitudinal edges between said faces,
    at least one of said faces having teeth for filing a kerf in a direction transverse to said face when reciprocated, and
    a shank for engagement by drive means to apply reciprocating motion to said blade;
    said guide comprising, means mountable to a bone to guide said file for filing a kerf extending in a direction transverse to said one face,
    a slide mounted for movement along and guided by said arm,
    said slide having means for holding said blade perpendicular to said slide while said file is reciprocated,
    said file filing a kerf in said bone when said slide is moved along said arm as said file is reciprocated.

10. An osteotomy instrument in accordance with claim 9 wherein said arm has a slot and said slide is slidable along and guided by said slot.

11. An osteotomy instrument in accordance with claim 9 further including means for adjusting the angle of said blade with respect to said slide, thereby to change the width of said kerf.

12. An osteotomy instrument in accordance with claim 9 further wherein said arm has pivot means securable to a bone, said arm being swingable about said pivot means.

13. An osteotomy instrument in accordance with claim 12 wherein at least one of said longitudinal edges of said file has teeth formed thereon for cutting a kerf edgewise through a bone when said file is reciprocated and said arm is swung about said pivot means.

14. Apparatus for performing arcuate osteotomies comprising a cutting guide and a bone cutting implement,
    said cutting guide comprising, an arm, a pivot pin extending from said arm and securable into a bone, said arm being swingable about said pivot pin, a slide mounted for guided movement along said arm, means on said slide for holding said cutting implement for cutting a kerf perpendicular to said arm, said slide being movable inwardly and outwardly along said arm to guide said cutting implement, said arm also presenting a stop which arrests inward movement of said slide so that when said arm is rotated about said pin, said cutting implement is moved along an arc of constant radius.

15. The apparatus of claim 14 wherein said guide further includes means for limiting the extent of rotation of said arm about said pivot pin, thereby to guide said cutting implement to form a tapered correction by moving said slide along said arm along first and second angular paths corresponding to the limits of rotation of said arm about said pivot pin.

16. The apparatus of claim 14 wherein said rotation limiting means is a transverse slot in said arm and a stop extending through said slot and into a bone, said arm being swingable about said pivot pin between angular positions at which said stop arrests the opposite ends of said slot.

17. The apparatus of claim 14 wherein said cutter is a file.

18. The apparatus of claim 14 wherein said cutter is a rotary burr.

19. The apparatus of claim 14 wherein said cutter is a reciprocating saw.

20. In the method of performing an arcuate osteotomy wherein an arcuate cut is made with a cutting implement across part of the width of a bone and a tapered correction is cut across the rest of the width of the bone, thereby severing the bone into two segments which can be rotated about the arcuate cut to close the correction and thereby straighten the bone, the improvement comprising, mounting a cutting guide for rotation about a pivot pin fixed to said bone, said guide presenting a guide track which extends outwardly from said pivot, moving a rotary burr cutter along said guide track to cut one side of said correction, swinging said guide about said pivot to a second angular position corresponding to a desired taper for the correction, and moving said rotary burr cutter along said guide track to cut a second side of said correction.

21. The improvement of claim 20 wherein said rotary burr cutter is held at a given position along said guide track as said guide is swung about said pivot pin thereby to cut said arcuate cut.

22. In a method of performing an arcuate osteotomy wherein an arcuate cut is sawn across part of the width of a bone and a correction extends across the rest of the width of the bone to an opposite side thereby severing the bone into two segments, and wherein the segments are then rotated about said arcuate cut and set in a desired new alignment, the improvement comprising, making said correction by filing a wedge-shaped kerf which extends between said arcuate cut and said opposite side of the bone.

23. The improvement of claim 22 wherein said correction is made by filing said kerf with a curved blade having a file cut on a curved face thereof.

24. The improvement of claim 22 wherein said correction is filed inwardly from said opposite side of the bone, said correction being made with a blade having a concave face with a file cut thereon.

25. The improvement of claim 22 wherein said arcuate cut is made by cutting with an edge of a curved blade, and said correction is cut by filing with a curved face of said blade.

26. The improvement of claim 25 wherein said blade is moved in a direction transverse to said curved face to file said correction.

27. The improvement of claim 25 wherein said correction is made before said arcuate cut, by filing it with a semicircularly curved blade having a file on a concave face thereof, and said arcuate cut is made from said correction.

28. The improvement of claim 23 wherein the path of said blade is guided by a guide fixed to said bone, said arcuate cut is made by swinging said guide around a pin fixed to said bone, said blade moving along a semicircular path, said blade having a radius of curvature equal to the radius of curvature of said path.

29. The improvement of claim 28 further wherein said blade is moved along a transverse path defined by said guide to make said correction.

30. The improvement of claim 29 wherein said guide is swung between angular movement limiting stops to guide said blade to cut a wedge-shaped correction.

31. The improvement of claim 22 wherein said kerf is wider than said arcuate cut.

* * * * *